United States Patent
Rangabhatla et al.

(10) Patent No.: US 10,561,583 B2
(45) Date of Patent: Feb. 18, 2020

(54) DENTAL CEMENT COMPOSITION

(71) Applicants: Gunneswara Subramanya Vara Prasad Rangabhatla, Bangalore (IN); Shrisha Belaldavara, Bangalore (IN); Ratna Phani Ayalasomayajula, Bangalore (IN)

(72) Inventors: Gunneswara Subramanya Vara Prasad Rangabhatla, Bangalore (IN); Shrisha Belaldavara, Bangalore (IN); Ratna Phani Ayalasomayajula, Bangalore (IN)

(73) Assignee: SHILPA MEDICARE LIMITED, Raichur, Karnataka ( * ) Notice: Subject to any disclaimer, the term of this patent is extended or adjusted under 35 U.S.C. 154(b) by 353 days.

(21) Appl. No.: 15/672,317

(22) Filed: Aug. 9, 2017

(65) Prior Publication Data
US 2019/0046418 A1 Feb. 14, 2019

(51) Int. Cl.
| | |
|---|---|
| *A61K 6/00* | (2006.01) |
| *A61K 6/06* | (2006.01) |
| *C04B 12/02* | (2006.01) |
| *A61K 6/04* | (2006.01) |
| *C04B 12/04* | (2006.01) |
| *A61K 6/033* | (2006.01) |
| *C04B 28/34* | (2006.01) |
| *C04B 111/00* | (2006.01) |

(52) U.S. Cl.
CPC .......... *A61K 6/0008* (2013.01); *A61K 6/0038* (2013.01); *A61K 6/033* (2013.01); *A61K 6/046* (2013.01); *A61K 6/0612* (2013.01); *C04B 12/027* (2013.01); *C04B 12/04* (2013.01); *C04B 28/34* (2013.01); *C04B 2111/00836* (2013.01)

(58) Field of Classification Search
CPC ..... A61K 6/0008; A61K 6/0612; A61K 6/033
See application file for complete search history.

(56) References Cited

U.S. PATENT DOCUMENTS 7,553,362 B2 * 6/2009 Lu .................. A61K 6/033
106/35
7,819,663 B2 * 10/2010 Bergaya .............. C04B 28/02
106/35

OTHER PUBLICATIONS

"Dental discoloration caused by bismuth oxide in MTA in the presence of sodium hypochlorite" Marina Angélica Marciano et al., Clin Oral Investing. Dec. 2015 ;19(9):2201-9.

* cited by examiner

*Primary Examiner* — C Melissa Koslow

(57) ABSTRACT

The present invention relates to dental cement composition that is more biocompatible and stimulates quicker healing of the damaged dental tissues. Specifically, the invention relates to dental cement composition comprising a combination of dental repair compounds consisting of nanoparticles of Tri-calcium Silicate ($Ca_3SiO_5$), Di-calcium Silicate ($Ca_2SiO_4$), Calcium Titanate ($CaTiO_3$) and Hydroxyapatite ($Ca_{10}(PO_4)_6(OH)_2$).

3 Claims, 3 Drawing Sheets

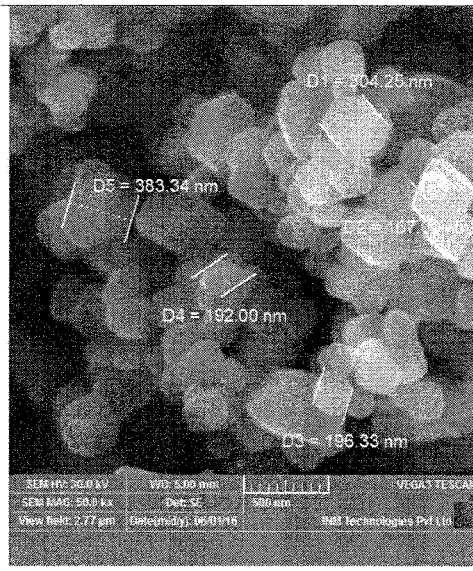 | 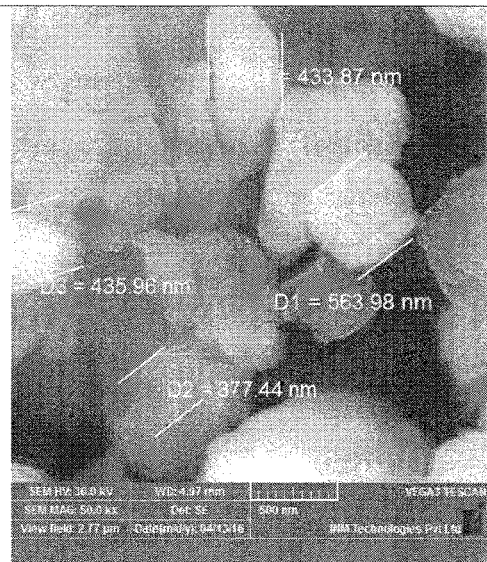

| Fig-1: Scanning electron microscopy of dental cement composition (Hybrid MTA of present invention) showing particle size ranging from 167-380nm at different locations (represented in solid lines showing the diameter of the particles in the figure) | Fig-2: Scanning electron microscopy of dental cement (MTA Plus-marketed sample) showing larger aggregates/lumps of particles with particles ranging from 377-563 nm at different locations (represented in solid lines showing the diameter of the particles in the figure)<br><br>PRIOR ART |

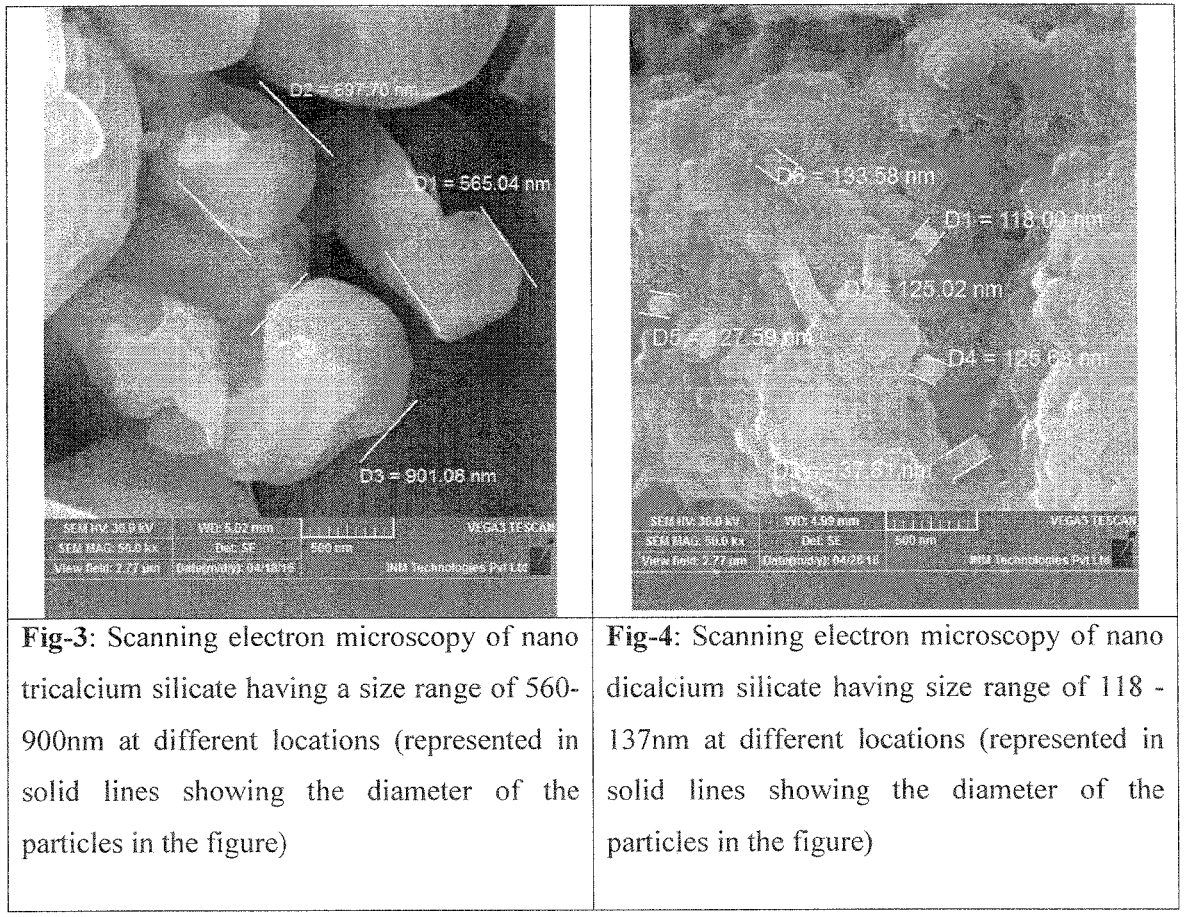

Fig-3: Scanning electron microscopy of nano tricalcium silicate having a size range of 560-900nm at different locations (represented in solid lines showing the diameter of the particles in the figure)

Fig-4: Scanning electron microscopy of nano dicalcium silicate having size range of 118 - 137nm at different locations (represented in solid lines showing the diameter of the particles in the figure)

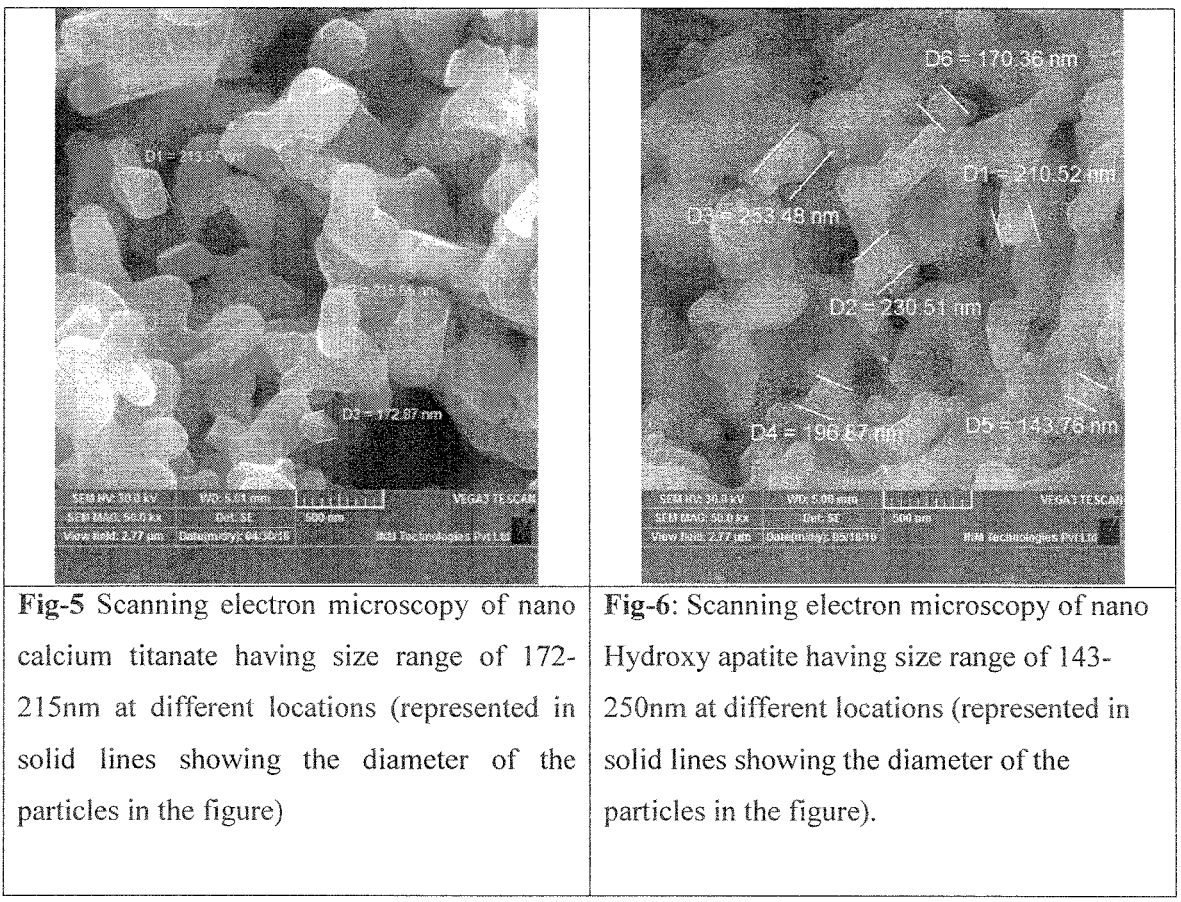

DENTAL CEMENT COMPOSITION

FIELD OF INVENTION

The present invention is related to dental compositions. More specifically discloses a fast-setting dental cement composition comprising combination of dental repair compounds consisting of Tri-calcium Silicate ($Ca_3SiO_5$), Di-calcium Silicate ($Ca_2SiO_4$), Calcium Titanate ($CaTiO_3$) and hydroxyapatite ($Ca_{10}(PO_4)_6(OH)_2$), wherein each of these compounds are in nanoparticulate form, and a hydration liquid.

BACKGROUND OF THE INVENTION

In most dental, in particular endodontic, procedures the achievement of a good seal between the tooth and the filling composition is very much essential in order to prevent bacterial recontamination of the root canal and ensure long-term clinical success. The presence of marginal gaps between the interfaces of retrofilling compositions and root dentin are sites of possible micro leakage and penetration of microorganisms and their toxins which disables the total integrity of the dental repair compounds.

The most common dental filling material that used is Gutta-Percha, which is a natural resin and a thermoplastic rubber. However, the non-adhesive character of Gutta-Percha and the irregularities on the internal surface of the root canal makes it difficult to seal off the root canal completely. In order to overcome this limitation, sealants are used along with Gutta-Percha. Numerous sealants have been known in the art, for example, epoxy resins, calcium hydroxide, and zinc oxide eugenol-based sealers. During the root canal filling process, such materials are first applied to the Gutta-Percha, which is then inserted into the root canal. Alternatively, they may be inserted using a file or reamer applicator, so that the spaces between the Gutta-Percha points and the root canal walls can be sealed. However, controlling the exact amount of the sealant and/or filling material within the root canal to avoid overextension or overfilling has long been a challenge for endodontists. For example, in case of overflow of root canal sealant from the apical foramen into the periradicular tissue during a root canal filling process, the excess material should be desirably tolerated by the surrounding tissue.

One of the drawbacks of conventional sealants is that they tend to be hydrophobic, making them incompatible with moist tissues within the root canal. Thus the hydrophilic nature of the root canal environment inhibits adequate penetration, complete wetting, and efficient adhesion of the hydrophobic sealant to the root canal walls. As a result, a poor seal is made between the Gutta-Percha and the root canal walls leading to re-entrance of microorganisms into the canal. In addition, overfilled Gutta-Percha and/or conventional sealant materials irritate the periapical soft tissues and do not stimulate healing and hard tissue formation. Moreover, and most importantly, Gutta-Percha and conventional sealants degrade during long-term exposure to fluids present in the oral cavity.

Mineral trioxide aggregate (MTA) (ProRoot MTA, Dentsply) is one commonly used dental cements that consists of at consists of 75% Portland cement, 20% bismuth oxide, and 5% gypsum by weight which is used as a root-filling material. Some difficulties are reported by clinicians when using MTA including poor handling characteristic and lengthy setting time.

White Mineral Trioxide Aggregate (WMTA) is another one of the commonly used dental cements, which is also used as a root-end filling material. While WMTA has many advantages including biocompatibility, good sealing ability, and antibacterial properties, it suffers from low pH resistance, which affects the microhardness, and long setting time. Conventional materials like calcium aluminates and bismuth oxide result in discoloration of the tooth. Bismuth oxide in the presence of sodium hypochlorite which is used as the irrigation solution results in discoloration of tooth, see Marina Angélica Marciano et al., Clin Oral Investig. 2015 December; 19(9):2201-9.

Therefore, in the light of the above discussion, there remains a need for a multi-purpose dental composition to be used in root canal treatments, root-end filling procedures, and pulp capping, which nullifies the drawbacks of aforementioned dental materials used for the same.

OBJECTS OF THE INVENTION

The objective of the present invention is to provide a dental cement composition that is more biocompatible and stimulates quicker healing of the damaged dental tissues.

Another objective of the present invention is to provide a dental cement composition that sets quicker in an aqueous environment and exhibits antimicrobial properties.

SUMMARY OF THE INVENTION

The inventors of the present invention have made the surprising discovery that the addition of nanoparticles of combination consisting of Calcium titanate and hydroxyapatite as a dental repair compound to the combination of dental repair compounds consisting nanoparticles of Tri-calcium Silicate ($Ca_3SiO_5$), Di-calcium Silicate ($Ca_2SiO_4$) resulted in dental cement compositions having fast-setting times i.e shortened setting times. Thus, the invention is directed to dental cement compositions, treatment methods, and manufacturing processes for improved dental cement compositions and dental repair procedures.

In one embodiment, the invention is drawn to a fast-setting dental cement composition comprising combination of dental repair compounds consisting of Tri-calcium Silicate ($Ca_3SiO_5$), Di-calcium Silicate ($Ca_2SiO_4$), Calcium Titanate ($CaTiO_3$) and hydroxyapatite ($Ca_{10}(PO_4)_6(OH)_2$), wherein each of these compounds are in nanoparticulate form.

In another embodiment, the invention is drawn to a fast-setting dental cement composition comprising combination of dental repair compounds consisting of Tri-calcium Silicate ($Ca_3SiO_5$), Di-calcium Silicate ($Ca_2SiO_4$), Calcium Titanate ($CaTiO_3$) and hydroxyapatite ($Ca_{10}(PO_4)_6(OH)_2$), wherein each of these compounds are in nanoparticulate form and a hydration liquid.

In another embodiment, the invention is drawn to methods of effecting dental repairs using the dental cement composition of the present invention as described above. Those dental repairs include but not limited to filling a tooth cavity, treating tooth decay, performing root canal therapy, apicoectomy and sealing a root perforation.

In yet another embodiment, the invention is drawn to a kit useful in the practice of dental repair, said kit comprising a packaged dental repair compounds [nanoparticles of Tri-calcium Silicate ($Ca_3SiO_5$), Di-calcium Silicate ($Ca_2SiO_4$), Calcium Titanate ($CaTiO_3$) and hydroxyapatite ($Ca_{10}(PO_4)_6$ $(OH)_2$)] and a packaged hydration liquid, and a set of instructions describing how to mix (e.g., in what proportions) the dental repair compound and a hydration liquid.

BRIEF DESCRIPTION OF DRAWINGS

A number of non-limiting embodiments of the present invention will be described by way of example with reference to the accompanying figures, in which:

FIG. 1 Scanning electron microscopy of dental cement composition (Hybrid MTA of present invention) showing particle size ranging from 167-380 nm at different locations (represented in solid lines showing the diameter of the particles in the figure)

FIG. 2 Scanning electron microscopy of dental cement (MTA Plus-marketed sample) showing larger aggregates/lumps of particles with particles ranging from 377-563 nm at different locations (represented in solid showing the diameter of the particles in the figure)

FIG. 3 Scanning electron microscopy of nano tricalcium silicate having a size range of 560-900 nm at different locations (represented in solid showing the diameter of the particles in the figure)

FIG. 4 Scanning electron microscopy of nano dicalcium silicate having size range of 118-137 nm at different locations (represented in solid showing the diameter of the particles in the figure)

FIG. 5 Scanning electron microscopy of nano calcium titanate having size range of 172-215 nm at different locations (represented in solid showing the diameter of the particles in the figure)

FIG. 6 Scanning electron microscopy of nano Hydroxy apatite having size range of 143-250 nm at different locations (represented in solid showing the diameter of the particles in the figure).

DETAILED DESCRIPTION OF THE INVENTION

Definitions

In the present text "nanoparticles or nanoparticulate" and other indicative terms indicates the particle size of less than 500 nm. In embodiments the "nanoparticles or nanoparticulate" have a particle size of about 0.5 nm to about 1000 nm, of about 1 nm to about 500 nm, and particularly of about 50 nm to about 500 nm. The particle size is defined herein as the average diameter of the "nanoparticles or nanoparticulate", as determined by SEM (scanning electron microscopy).

In the present text "hydration liquid" and other indicative terms indicates any vehicle such as liquid base, gel base, suspension bases or emulsion bases that are mixed with the combination of dental repair compounds to form the dental cement composition.

The present invention provides, a fast-setting dental cement composition comprising combination of dental repair compounds consisting of Tri-calcium Silicate ($Ca_3SiO_5$), Di-calcium Silicate ($Ca_2SiO_4$), Calcium Titanate ($CaTiO_3$) and hydroxyapatite ($Ca_{10}(PO4)_6 (OH)_2$), wherein each of these compounds are in nanoparticulate form.

In one embodiment the invention, provides a fast-setting dental cement composition comprising combination of dental repair compounds consisting of Tri-calcium Silicate ($Ca_3SiO_5$), Di-calcium Silicate ($Ca_2SiO_4$), Calcium Titanate ($CaTiO_3$) and hydroxyapatite ($Ca_{10}(PO_4)_6(OH)_2$), wherein each of these compounds are in nanoparticulate form and a hydration liquid.

In another embodiment, the invention provides a fast-setting dental cement composition comprising combination of dental repair compounds consisting of about 35% to about 85% Tri-calcium Silicate ($Ca_3SiO_5$), about 2% to about 8% Di-calcium Silicate ($Ca_2SiO_4$), about 5% to about 15% Calcium Titanate ($CaTiO_3$) and about 10% to about 40% Hydroxyapatite ($Ca_{10}(PO_4)_6(OH)_2$) by weight based on the total weight of the dental repair compounds, wherein each of these compounds are in nanoparticulate form.

In a further embodiment, the invention provides a fast-setting dental cement composition comprising combination of dental repair compounds consisting of about 35% to about 85% Tri-calcium Silicate ($Ca_3SiO_5$), about 2% to about 8% Di-calcium Silicate ($Ca_2SiO_4$), about 5% to about 15% Calcium Titanate ($CaTiO_3$) and about 10% to about 40% Hydroxyapatite ($Ca_{10}(PO_4)_6(OH)_2$) by weight based on the total weight of the dental repair compounds, wherein each of these compounds are in nanoparticulate form and a hydration liquid.

Dental Repair Compounds

A main constituent of the dental cement composition are dental repair compounds. The dental repair compounds of the present invention consist of combination of Tri-calcium Silicate ($Ca_3SiO_5$), Di-calcium Silicate ($Ca_2SiO_4$), Calcium Titanate ($CaTiO_3$) and hydroxyapatite ($Ca_{10}(PO_4)_6(OH)_2$). The dental repair compounds typically constitute such as about 50% to about 95% by weight based on the total weight of the dental cement composition.

According to some embodiments, the dental cement composition comprises the combination of dental repair compounds consisting of about 35% to about 85% of Tri-calcium Silicate ($Ca_3SiO_5$) by weight based on the total weight of dental repair compounds.

According to some embodiments, the dental cement composition comprises the combination of dental repair compounds consisting of about 2% to about 8% Di-calcium Silicate ($Ca_2SiO_4$) by weight based on the total weight of dental repair compounds.

The dental cement composition of the present invention comprises the combination of about 35% to about 85% Tri-calcium Silicate ($Ca_3SiO_5$), about 2% to about 8% Di-calcium Silicate ($Ca_2SiO_4$), more than about 5% of Calcium Titanate ($CaTiO_3$) and more than about 10% Hydroxyapatite ($Ca_{10}(PO_4)_6(OH)_2$) by weight based on the total weight of dental repair compounds.

In order to obtain the dental cement composition with shorter setting times, the inventors of the present invention have selected the calcium titanate, preferably in the range of about 5% to about 15% by weight based on the total weight of dental repair compounds and in combination with Hydroxyapatite in the range of about 10% to about 40% by weight based on the total weight of dental repair compounds, without the aluminate content. Furthermore, by using such fast setting dental repair compounds consisting the combination of calcium titanate and Hydroxyapatite, it is possible to mix the combination of dental repair compounds combination with hydration liquid to get a favorable consistency and practical setting time of less than 15 minutes.

In embodiments of the present invention, the dental cement composition comprises the dental repair compounds, wherein each compound has a particle surface area of about 1 to about 50 $m^2/g$.

In one embodiment of the present invention, the dental cement composition comprises the combination of dental repair compounds consisting of combination of Tri-calcium Silicate ($Ca_3SiO_5$), Di-calcium Silicate ($Ca_2SiO_4$), Calcium Titanate ($CaTiO_3$) and Hydroxyapatite ($Ca_{10}(PO_4)_6(OH)_2$), wherein each of these compounds have a particle surface area of about 1 to about 50 m²/g.

Hydration Liquid

The material further comprises a hydration liquid. The hydration liquid is typically mixed with the combination of dental repair compounds prior to use of the dental cement composition. The hydration liquid constitutes of about 5% to 50% by weight based on the total weight of the dental cement composition. In some embodiments, the hydration liquid constitutes of about 10% to 30%, such as about 15% to 25% by weight based on the total weight of the dental cement composition. The main constituents of the hydration liquid is purified water.

The one or more super plasticizer constitutes of about 0.001% to about 10% by weight of the hydration liquid, such as about 0.1% to about 8%, example about 0.2% to about 0.5% by weight of the hydration liquid. In some embodiments, the one or more super plasticizers are included in the hydration liquid, however it also possible that super plasticizer is added as powder to the dental repair compounds powder mix as a salt or freeze dried components. This allows the use of fast-setting dental cement compounds with only water as the hydration liquid.

The superplasticizers are well-defined and chemically different from the older plasticizer products. Plasticizers for dental cement compositions have been made from lignosulfonates, and superplasticizers were later developed from sulfonated naphthalene condensate and sulfonated melamine formaldehyde. The new and more biocompatible polyacid-based superplasticizers work on dispersed powder particles by steric dispersion and steric stabilization, instead of only electrostatic repulsion, which is more powerful than only electrostatic repulsion. The new generation of polycarboxylate-based superplasticizers such as such as sodium polycarboxylate reduces effectively the surface forces and/or adhesion between particles in fast-setting dental cement compositions and enable thereby a reduction of water-dental repair compounds powder ratio.

Furthermore, it is also possible, but not mandatory that the hydration liquid comprises one or more soluble additives in an amount of more than about 0.001% by weight of the hydration liquid. Practically, hydration liquid with admixtures, superplasticizers and further soluble salts are added to a bottle and shaken until all salts have been dissolved and the hydration liquid is ready for use.

Examples of such soluble additives in the hydration liquid are water soluble polymers selected from polyacrylic acid and polyvinyl alcohol to form the gel compositions.

Further the soluble additives in the hydration liquid are potassium nitrate and sodium fluoride.

In one embodiment, the hydration liquid comprises i) 0.001-10% by weight of the liquid of one or more superplasticizers; and ii) more than 0.001%, such as 0.001-10%, e.g. 0.2-5.0%, by weight of the liquid of one or more soluble additives.

Fine Particulation

The dental repair compounds in the present invention consists of discrete and individual particulate fractions of suitable size i.e fine nanoparticles having a particle size of about 0.5 nm to about 1000 nm, of about 1 nm to about 500 nm, and particularly of about 50 nm to about 500 nm.

Preparation of Combination of Dental Repair Compounds

Each of dental repair compounds as disclosed above are mixed together in any order and are stored at pre-determined temperature, pressure and humidity (37° C., low humidity environment) for a predetermined period of time.

Regulation of Setting Time

The setting time is controlled in a specific time range which is practical for many dental application i.e about less than 15 minutes. The inventors of the present invention have surprisingly found that the setting time has been reduced to about less than 15 minutes, preferably about 10 minutes by addition of the dental repair compounds consisting the combination of calcium titanate and hydroxyapatite.

Preparation of Dental Cement Composition

The combination of dental repair compounds and the hydration liquid here is either mixed into a paste on a mixing pad by using a hand spatula for 20 to 60 seconds.

Kits

In embodiments of the invention, the invention provides a kit useful in the practice of dental repair, said kit comprising a packaged dental repair compounds [nanoparticles of Tri-calcium Silicate ($Ca_3SiO_5$), Di-calcium Silicate ($Ca_2SiO_4$), Calcium Titanate ($CaTiO_3$) and hydroxyapatite ($Ca_{10}(PO_4)_6(OH)_2$)] and a packaged hydration liquid, and a set of instructions describing how to mix (e.g., in what proportions) the dental repair compound and a hydration liquid.

Use of Dental Cement Composition for Prevention and Treatment of Disease

In embodiments of the invention, the invention provides the methods of effecting dental repairs using the dental cement composition of the present invention as described above. Those dental repairs include but not limited to filling a tooth cavity, treating tooth decay, performing root canal therapy, apicoectomy and sealing a root perforation.

In further aspects, the invention relates to the possible use of fast-setting dental cement compositions for prevention disease, stimulation of hard tissue regeneration, inhibition of resorptions and treatments of endodontic disease, traumas, peridontal disease, orofacial conditions, and bone defects.

Preparation of Combination of Dental Repair Compounds

A detailed breakup of the combinations of dental repair compound present in the dental cement composition is tabulated in Table 1.

TABLE 1

| Ingredient | Molecular Formula | Weight % |
| --- | --- | --- |
| Tri-calcium Silicate | $Ca_3SiO_5$ | 35%-85% |
| Di-calcium Silicate | $Ca_2SiO_4$ | 2%-8% |
| Calcium Titanate | $CaTiO_3$ | 5%-15% |
| Hydroxyapatite | $Ca_{10}(PO_4)_6(OH)_2$ | 10%-40% |

In order to prepare the combination of dental repair compounds, each dental repair compound thereof is mixed together in any order and are stored at pre-determined temperature, pressure and humidity (37° C., low humidity environment) for a predetermined period of time. The particle size of the nanoparticles of combination of the dental repair compounds as prepared is shown in FIG. 1, range between 50 nm to 500 nm.

Comparison of Surface Area of MTA Plus (Marketed Sample) and MTA Hybrid (Present Invention)

Studies show that the size and surface area of the particles of the combination of dental repair compounds play an important role in physical and chemical properties thereof. More particularly, the particles with greater surface area exhibit faster reactivity and have lower porosity, which is inversely proportional to microhardness. The dimensional characteristics of combination of dental repair compounds of the present invention related to the specific surface area are depicted in the following Table. 2, wherein the characteristics are determined using Brunauer, Emmett, and Teller (BET) theory.

TABLE 2

| S. No | Component | Surface area (m$^2$/g) |
|---|---|---|
| 1 | MTA Plus (Market sample) | 1.0992 |
| 2 | Hybrid MTA (as proposed in present invention) | 5-50 |
| | Individual components of Hybrid MTA | |
| 1 | Tricalcium Silicate | 1-50 |
| 2 | Dicalcium silicate | 1-50 |
| 3 | Calcium titanate | 1-50 |
| 4 | Hydroxyapatite | 1-50 |

Setting Time of MTA Plus (Marketed Sample) and MTA Hybrid (Present Invention)

The setting time of MTA Plus (marketed sample) was found to 1 hour, whereas setting time of MTA hybrid (Present invention) was found to be 10 minutes.

We claim:

1. A fast-setting dental cement composition comprising combination of dental repair compounds consisting of about 35% to about 85% Tri-calcium Silicate ($Ca_3SiO_5$), about 2% to about 8% Di-calcium Silicate ($Ca_2SiO_4$), about 5% to about 15% Calcium Titanate ($CaTiO_3$) and about 10% to about 40% Hydroxyapatite ($Ca_{10}(PO_4)_6(OH)_2$) by weight based on the total weight of the dental repair compounds, wherein each of these compounds are in nanoparticulate form.

2. A fast-setting dental cement composition according to claim 1, wherein nanoparticles have a particle size of about 50 nm to about 500 nm.

3. A fast-setting dental cement composition according to claim 1, wherein nanoparticles have the particle surface area of about 1 to about 50 m$^2$/g.

* * * * *